(12) United States Patent
Hatanaka et al.

(10) Patent No.: US 8,293,936 B2
(45) Date of Patent: Oct. 23, 2012

(54) METHOD FOR PRODUCING N-PROPYL ACETATE

(75) Inventors: Shigeru Hatanaka, Oita (JP); Masayuki Fujimoto, Kitsuki (JP)

(73) Assignee: Showa Denko Kabushiki Kaisha, Tokyo (JP)

( * ) Notice: Subject to any disclaimer, the term of this patent is extended or adjusted under 35 U.S.C. 154(b) by 78 days.

(21) Appl. No.: 12/993,224

(22) PCT Filed: May 20, 2009

(86) PCT No.: PCT/JP2009/059285
§ 371 (c)(1),
(2), (4) Date: Nov. 17, 2010

(87) PCT Pub. No.: WO2009/142245
PCT Pub. Date: Nov. 26, 2009

(65) Prior Publication Data
US 2011/0065951 A1    Mar. 17, 2011

(30) Foreign Application Priority Data

May 21, 2008 (JP) .................................. 2008-133403

(51) Int. Cl.
*C07C 67/283* (2006.01)
(52) U.S. Cl. ...................................................... 560/265
(58) Field of Classification Search .................... None
See application file for complete search history.

(56) References Cited

U.S. PATENT DOCUMENTS
6,936,730 B1    8/2005  Ohga et al.

FOREIGN PATENT DOCUMENTS
| JP | 56-071040 A | 6/1981 |
| JP | 2552161 B2 | 8/1989 |
| JP | 02-091045 A | 3/1990 |
| JP | 09-194427 A | 7/1997 |
| WO | 00/64852 A1 | 11/2000 |

*Primary Examiner* — Paul A Zucker
(74) *Attorney, Agent, or Firm* — Sughrue Mion, PLLC (57) ABSTRACT

Provided is a method for producing n-propyl acetate capable of suppressing the deterioration of a hydrogenation catalyst to such an extent that the catalyst can be industrially used, for example, in the case where n-propyl acetate is produced by performing a hydrogenation reaction in the presence of the hydrogenation catalyst using, as a raw material liquid, a liquid containing allyl acetate or the like which has been produced from propylene, oxygen and acetic acid and obtained using a purification process such as distillation. In such a method for producing n-propyl acetate, the concentration of a formyl group-containing compound (such as acrolein, propionaldehyde or 2-methylcrotonaldehyde) and the concentration of an acryloyloxy group-containing compound (such as acrylic acid or allyl acrylate) in the raw material liquid are respectively set to 100 ppm by mass or less. As a result, the deterioration of the hydrogenation catalyst can be suppressed to such an extent that the catalyst can be industrially used.

18 Claims, 2 Drawing Sheets

METHOD FOR PRODUCING N-PROPYL ACETATE

TECHNICAL FIELD

The present invention relates to a method for producing n-propyl acetate by a hydrogenation reaction of a raw material liquid containing allyl acetate.

The present application claims priority on Japanese Patent Application No. 2008-133403 filed in Japan on May 21, 2008, the content of which is incorporated herein by reference.

BACKGROUND ART

Conventionally, saturated esters such as n-propyl acetate, isobutyl acetate and n-butyl acetate have been commonly used as solvents and reaction solvents and are industrially important compounds. These saturated esters are generally produced by an esterification reaction resulting from condensation of a corresponding alcohol and carboxylic acid.

However, in such esterification reactions, the reaction equilibrium cannot be shifted to the product (saturated esters) side unless water as a by-product is removed from the system, and it is industrially difficult to obtain a high raw material conversion rate and reaction rate. Since the latent heat of vaporization of water is much higher than that of other organic compounds, there is also the difficulty of consuming a large amount of energy during the separation of water by distillation.

On the other hand, unsaturated esters, which contain an unsaturated group such as an allyl group, a methacrylic group or a vinyl group, in the alcohol portion of an ester, can be produced industrially through an oxidative carboxylation reaction or the like between a corresponding olefin and a carboxylic acid.

In particular, it is well known that unsaturated group-containing esters can be produced by reacting a corresponding olefin, oxygen and a carboxylic acid in the gas phase in the presence of a palladium catalyst, and there are numerous known documents regarding this production. For example, PTL 1 describes how allyl acetate can be produced industrially with an extremely high yield and high space-time yield by reacting propylene, oxygen and acetic acid in the presence of a palladium catalyst in the gas phase.

In addition, there are numerous known documents describing a reaction of adding hydrogen to a carbon-carbon double bond of an unsaturated group-containing ester such as allyl acetate, that is, a hydrogenation reaction (also referred to as "hydrogen addition").

For example, PTL 2 discloses a method of producing n-propyl acetate by hydrogenating allyl acetate using a nickel catalyst as a catalyst for the hydrogenation reaction, in other words, a hydrogenation catalyst. PTL 3 describes a method of producing n-propyl acetate by using a silica-supported palladium catalyst, an alumina-supported palladium catalyst, a sponge nickel or the like. According to the PTL 3, an allyl acetate conversion rate of substantially 100% can be achieved, while an n-propyl acetate selectivity of 99.0% or more is also achieved. Here, PTL 3 describes that in the case of synthesizing allyl acetate by passing a raw material gas containing propylene, oxygen and acetic acid in the presence of a palladium catalyst in the gas phase, the reactor outlet gas thus obtained is cooled and separated into a non-condensed component and a condensed component, and the crude allyl acetate liquid obtained as the condensed component is distilled to obtain an allyl acetate-containing liquid containing allyl acetate from the top of the column. When this allyl acetate-containing liquid is used as a raw material liquid and is hydrogenated, the target product, n-propyl acetate, can be obtained.

On the other hand, it is also known that when allyl acetate is synthesized by reacting propylene, oxygen and acetic acid in the presence of a palladium catalyst in the gas phase, by-products are produced, and for example, PTL 4 describes acrolein and diacetates (allylidene diacetate: $CH_2=CH\_CH(-OCOCH_3)_2$, 1,3-diacetoxypropene, and the like) as the by-products included in the condensed component.

Citation List

[Patent Literature]

[PLT 1] Japanese Unexamined Patent Application Publication No. 2-91045

[PLT 2] Japanese Unexamined Patent Application Publication No. 9-194427

[PLT 3] Pamphlet of International Patent Application No. WO 00/064852

[PLT 4] Japanese Patent Publication No. 2552161

SUMMARY OF INVENTION

Technical Problem

However, when conventional methods such as described in PTL 3 are employed, that is, when n-propyl acetate is produced by performing a hydrogenation reaction in the presence of the hydrogenation catalyst using, as a raw material liquid, an allyl acetate-containing liquid which has been produced from propylene, oxygen and acetic acid and obtained using a purification process such as distillation, there has been a problem that deterioration of the hydrogenation catalyst occurs conspicuously and rapidly.

The invention was made under such circumstances, and it is an object of the invention to suppress the deterioration of a hydrogenation catalyst to such an extent that the catalyst can be industrially used, for example, in the case where n-propyl acetate is produced by performing a hydrogenation reaction in the presence of the hydrogenation catalyst using, as a raw material liquid, an allyl acetate-containing liquid or the like which has been produced from propylene, oxygen and acetic acid and obtained using a purification process such as distillation.

Solution to Problem

As a result of the investigations made by the inventors of the present invention, it was found that the allyl acetate-containing liquid described above contains, as by-products, a formyl group-containing compound such as acrolein, propionaldehyde or 2-methylcrotonaldehyde, or an acryloyloxy group-containing compound such as acrylic acid or allyl acrylate or the like, and the inventors found that when a hydrogenation reaction is carried out using an allyl acetate-containing liquid containing these compounds at or above certain concentrations as a raw material, deterioration of the hydrogenation catalyst becomes conspicuous and rapid, that is, these by-products are catalyst poisoning substances of hydrogenation reactions. The inventors then conceived that if the concentrations of these by-products contained in the raw material liquid are decreased to a certain level or less, deterioration of the hydrogen catalyst during the hydrogenation reaction can be suppressed, thus completing the invention. Thus, the invention relates to the following items [1] to [6].

[1] A method for producing n-propyl acetate, including subjecting a raw material liquid containing allyl acetate to a hydrogenation reaction, wherein the concentration of a formyl group-containing compound and the concentration of an acryloyloxy group-containing compound in the raw material liquid are respectively 100 ppm or less by mass.

[2] The method for producing n-propyl acetate according to [1], wherein the raw material liquid contains an allyl acetate-containing liquid which is produced from propylene, oxygen and acetic acid.

[3] The method for producing n-propyl acetate according to [1] or [2], wherein the formyl group-containing compound is at least one selected from acrolein, propionaldehyde and 2-methylcrotonaldehyde.

[4] The method for producing n-propyl acetate according to [1] or [2], wherein the acryloyloxy group-containing compound is acrylic acid and/or allyl acrylate.

[5] The method for producing n-propyl acetate according to any one of [1] to [4], wherein the hydrogenation reaction uses, as a hydrogenation catalyst, a compound containing at least one element selected from the group consisting of the elements of Group 8, Group 9 and Group 10 in the Periodic Table.

[6] The method for producing n-propyl acetate according to [5], wherein the hydrogenation catalyst is a compound containing at least one selected from the group consisting of palladium, rhodium, ruthenium, nickel and platinum.

Advantageous Effects of Invention

According to the invention, for example, in the case where n-propyl acetate is produced by performing a hydrogenation reaction in the presence of a hydrogenation catalyst using, as a raw material liquid, an allyl acetate-containing liquid or the like which has been produced from propylene, oxygen and acetic acid and obtained using a purification process such as distillation, deterioration of the hydrogenation catalyst can be suppressed to such an extent that the catalyst can be industrially used. Therefore, the frequency of catalyst exchange can be reduced, and the production cost for n-propyl acetate can be lowered.

DESCRIPTION OF EMBODIMENTS

The method for producing n-propyl acetate of the invention is a method of producing n-propyl acetate by subjecting a raw material liquid containing allyl acetate to a hydrogenation reaction, in which method the concentration of a formyl group-containing compound and the concentration of an acryloyloxy group-containing compound in the raw material liquid are respectively set to 100 ppm by mass or less.

The raw material liquid is not particularly limited so long as it contains allyl acetate, but the invention will be described in detail with reference to drawings, by taking an example of using, as the raw material liquid, an allyl acetate-containing liquid which has been produced from propylene, oxygen and acetic acid and obtained using a purification process such as distillation, and performing a hydrogenation reaction using the liquid.

<Production of Allyl Acetate Using Propylene, Oxygen and Acetic Acid as Raw Materials>

Figure 1:
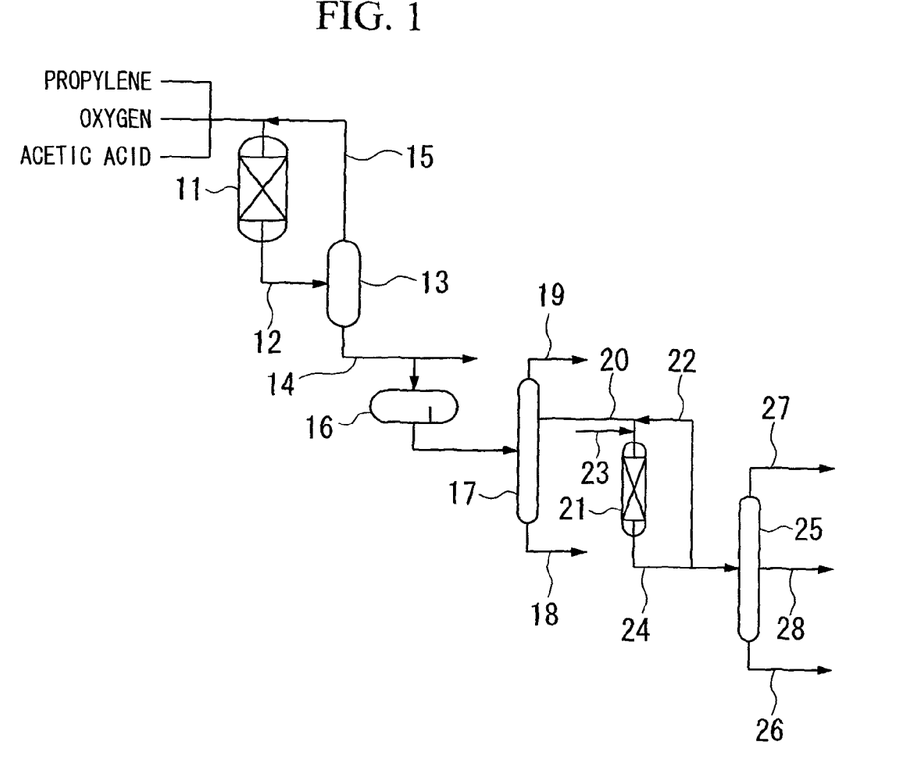
FIG. 1 is a process flow diagram showing an example of the process for producing n-propyl acetate by subjecting a raw material liquid containing allyl acetate to a hydrogenation reaction.

The reaction formula for the production of allyl acetate using propylene, oxygen and acetic acid as raw materials is represented by the following formula (1). When allyl acetate is produced by this reaction, as shown in FIG. 1, a raw material gas containing propylene, oxygen and acetic acid is first supplied to a reactor 11 packed with a catalyst.

[Chem. 1]

$$CH_2=CH-CH_3 + \tfrac{1}{2}O_2 + CH_3COOH \rightarrow CH_2=CH-CH_2-OCOCH_3 + H_2O \quad (1)$$

There are no particular limitations on the propylene used herein as the raw material gas. Although lower saturated hydrocarbons such as propane or ethane may be mixed in the raw material gas, it is preferable to use highly pure propylene. Moreover, there are also no particular limitations on the oxygen. Oxygen may be diluted with an inert gas such as nitrogen or carbon dioxide gas, and for example, air may also be used. However, as shown in the drawings, in the case of circulating unreacted reaction gas which has not been used in the reaction, to the reactor 11 as a non-condensed component 15 that will be described later, it is preferable to use highly pure oxygen, and particularly oxygen having a purity of 99% or more.

The raw material gas supplied to the reactor 11 contains acetic acid, propylene and oxygen, and may further contain, if necessary, nitrogen, carbon dioxide, a rare gas or the like as a diluent. Preferable proportions of various gases in the total amount of the raw material gas are 4 vol % to 20 vol % more preferably 6 vol % to 10 vol % for acetic acid; and 5 vol % to 50 vol %, and even more preferably 10 vol % to 40 vol % for propylene.

The ratio of acetic acid, propylene and oxygen in terms of molar ratio is preferably such that acetic acid:propylene:oxygen=1:0.25 to 13:0.15 to 4, and more preferably such that acetic acid:propylene:oxygen=1:1 to 7:0.5 to 2.

The catalyst packed in the reactor 11 may be any catalyst capable of obtaining allyl acetate by reacting propylene, acetic acid and oxygen. A preferable catalyst is a supported solid catalyst containing the following components (a) to (c):
(a) palladium,
(b) a compound having at least one element selected from copper, lead, ruthenium and rhenium, and
(c) at least one compound selected from alkali metal acetate and alkaline earth metal acetate.

Although palladium having any valence may be used as the component (a), metallic palladium is preferable. The "metallic palladium" as used herein is palladium having a valence of 0. Metallic palladium can be usually obtained by reducing palladium ions having a valence of 2 and/or 4 using a reducing agent such as hydrazine or hydrogen. At this time, it is not required that all of the palladium be in the metal form.

There are no particular limitations in the raw material of the component (a). Not only metallic palladium can certainly be used, but also a palladium salt that can be converted to metallic palladium can be used. Examples of palladium salts that can be converted to metallic palladium include, but are not limited to, palladium chloride, palladium sodium chloride, palladium nitrate and palladium sulfate.

The ratio of the carrier and the component (a) as a mass ratio is preferably such that the ratio of carrier:component (a)=1:0.1 to 5.0, and more preferably such that the ratio of carrier:component (a)=1:0.3 to 1.0.

A salt that is soluble in water, such as a nitrate, carbonate, sulfate, organic acid salt or halide having at least one element selected from the group consisting of copper, lead, ruthenium and rhenium, can be used as the component (b). Among these, chlorides are preferable since they are readily available and have excellent water solubility. A preferable element among the elements mentioned above may be copper. Examples of copper chloride include, but are not limited to, cuprous chloride, cupric chloride, copper acetate, copper nitrate, copper acetylacetonate and copper sulfate.

The ratio between the component (a) and the component (b) as a molar ratio is preferably such that component (a):component (b)=1:0.05 to 10, and more preferably such that component (a):component (b)=1:0.1 to 5.

A preferable example of the component (c) is an alkali metal acetate, and specific examples thereof include acetates of lithium, sodium and potassium. More preferable examples include sodium acetate and potassium acetate, and potassium acetate is the most preferable.

Although there are no particular limitations on the supported amount of the component (c), the supported amount is preferably 1 to 30% by mass based on 100 parts by mass of the carrier. Furthermore, in order to obtain a desired supported amount, an acetate of an alkali metal may be added to the reactor 11 according to a method of, for example, adding the acetate to the raw material gas in the form of an aqueous solution or acetic acid solution.

There are no particular limitations on the carrier that supports the catalyst component, and any porous material generally used as a carrier may be used. Preferable examples of the support include silica, alumina, silica-alumina, diatomaceous earth, montmorillonite and titania, while silica is more preferable. Furthermore, there are no particular limitations on the shape of the carrier. Specific examples of the support shape include, but are not limited to, a powder form, a spherical form and a pellet form.

Although there are no particular limitations on the particle diameter of the carrier, the particle diameter is preferably 1 to 10 mm, and more preferably 3 to 8 mm. In the case of carrying out the reaction with the catalyst packed in a tubular reactor, if the particle diameter is less than 1 mm, there is a concern that large pressure loss occurs when the raw material gas is allowed to flow through the reactor, and thereby gas circulation cannot be effectively achieved. Furthermore, if the particle diameter exceeds 10 mm, there is a concern that the raw material gas is unable to diffuse into the inside of the catalyst, and thereby the catalyzed reaction no longer proceeds effectively.

The pore structure of the carrier is such that the pore diameter is preferably 1 nm to 1000 nm, and more preferably between 2 nm and 800 nm.

There are no particular limitations on the method of supporting the component (a), component (b) and component (c) onto the carrier, and any method may be used for the supporting.

A specific example may be a method in which an aqueous solution of the component (a) such as a palladium salt and component (b) is impregnated into a carrier, and then the impregnated support is treated with an aqueous solution of an alkaline metal salt. At this time, it is preferable to carry out an alkali treatment without drying the carrier impregnated with the catalyst liquid. The time for a treatment with an aqueous solution of an alkaline metal salt is the amount of time required for the salt of the catalyst component impregnated in the carrier to be completely converted to a compound that is insoluble in water, and usually, 20 hours is sufficient.

Next, the metal salt of the catalyst component which has been precipitated on the surface layer of the catalyst support by the alkali metal salt treatment, is treated with a reducing agent to obtain a metal having a zero valence. The reduction treatment is carried out, for example, in a liquid state by adding a reducing agent such as hydrazine or formalin. Subsequently, the catalyst carrier is rinsed with water until chlorine ions and the like are no longer detected, followed by drying, and then an alkali metal acetate is supported on the catalyst support. The resultant is further dried. Supporting can be achieved by the method described above, but the method is not limited thereto.

There are no particular limitations on the reaction form used to carry out the reaction between propylene, oxygen and acetic acid in the presence of catalyst, and a conventionally known reaction form can be selected. In general, there is an optimal method for the catalyst used, and it is preferable to carry out the reaction in that optimal form. For example, in the case of using the supported solid catalyst described above, it is advantageous, in terms of practical use, to employ a fixed bed flow reaction in which the catalyst is packed in the reactor 11 as the reaction form.

Although there are no particular limitations on the material of the reactor 11, the reactor is preferably constituted of a material having corrosion resistance.

There are no particular limitations on the reaction temperature when the raw material gas is supplied into the reactor 11 and reacted. The reaction temperature is preferably 100° C. to 300° C., and more preferably 120° C. to 250° C.

There are no particular limitations on the reaction pressure. From the viewpoint of the facilities, a reaction pressure of 0.0 MPaG to 3.0 MPaG (gauge pressure) is practically advantageous, while a pressure of 0.1 MPaG to 1.5 MPaG is more preferable.

It is also preferable to pass the raw material gas through the catalyst in the standard state at a spatial velocity of 10 $hr^{-1}$ to 15,000 $hr^{-1}$, and particularly preferably 300 $hr^{-1}$ to 8000 $hr^{-1}$.

When the raw material gas is supplied to the reactor 11 under such conditions, a reactor outlet gas 12 which contains allyl acetate thus produced is obtained. Subsequently, this reactor outlet gas 12 is sent to a condensed component separation tank 13, and from the bottom of the condensed component separation tank 13, a crude allyl acetate liquid 14 containing allyl acetate, acetic acid and water as main components is obtained as the condensed component, while from the top, a non-condensed component 15 containing propylene, oxygen and carbon dioxide gas as main components is obtained. The non-condensed component 15 is preferably recycled as a reaction raw material from the top of the condensed component separation tank 13 to the reactor 11, as shown in the diagram.

Furthermore, an absorption column using acetic acid and water as an absorbent liquid may be provided, instead of providing the condensed component separation tank 13.

<Purification of crude allyl acetate liquid and production of n-propyl acetate>

Next, the crude allyl acetate liquid 14 is purified, and thereby impurities such as by-products are removed.

Specifically, as shown in FIG. 1, a part or the entire amount of the crude allyl acetate liquid 14 is supplied to an oil-water separation tank 16, and the oil layer containing a high concentration of allyl acetate is supplied to a first distillation column 17.

Then, a first distillation column bottom liquid 18 containing a high concentration of high-boiling point components such as acetic acid, acrylic acid, allyl acrylate and diacetates, and a first distillation column top liquid 19 containing a high concentration of low-boiling point components such as acrolein, propionaldehyde and water are respectively taken out and removed. These removed liquids may be used as fuel for a boiler, or may be returned to the allyl acetate production process and recycled.

Meanwhile, from a column middle tray of the first distillation column 17, a first distillation column middle tray distillate liquid, that is, an allyl acetate-containing liquid 20 is obtained. The purity of allyl acetate of this allyl acetate-containing liquid 20 is usually 95% or greater. Furthermore, the concentration of acrolein, propionaldehyde, 2-methylcrotonaldehyde, acrylic acid and allyl acrylate contained in the allyl acetate-containing liquid 20 may vary with the reaction conditions for the allyl acetate production process or the distillation conditions in the first distillation column 17, but the concentration is usually 0.1% by mass to 1.0% by mass in total.

Hereinafter, the conventional operation conditions for the first distillation column 17 will be described. The first distillation column 17 is operated under an operation pressure of atmospheric pressure+α, and the allyl acetate-containing liquid 20 which has its purity increased in a temperature range of 100° C. to 110° C. is distilled out from the column middle tray. From the column bottom, the first distillation column bottom liquid 18 containing acetic acid as a main component is pulled out at a column bottom temperature of 120° C. to 140° C. Furthermore, the component from the distillation column top is condensed in a condenser (not shown in the diagram) and is converted to a first distillation column top liquid 19. A portion of the liquid may be returned to the first distillation column 17. At this time, the first distillation column top liquid 19 is separated into two layers such as an aqueous layer and an oily layer, and the layers may be respectively returned as refluxes. The first distillation column 17 is usually constituted of an actual tray number in the range of 20 trays to 80 trays, and the column is operated at a reflux ratio in the range of 1 to 200.

The allyl acetate-containing liquid 20 thus obtained is subsequently transported to a hydrogenation reactor 21 which is packed with a hydrogenation catalyst, and is mixed with a recycle liquid 22 that is separately returned to the hydrogenation reactor 21 and a solvent that is inert to hydrogenation reactions (hereinafter, referred to as diluting solvent; not shown in the diagram) to be taken as a raw material liquid. This raw material liquid is allowed to undergo a hydrogenation reaction as shown in the following formula (2), under the action of hydrogen that is included in a feed gas 23, and thus n-propyl acetate is produced. In the depicted example, a portion of the n-propyl acetate thus produced is included in the recycle liquid 22 and is recycled into the hydrogenation reactor 21 as a diluting solvent, while the rest is included in a hydrogenation reaction liquid 24 and supplied to a second distillation column 25. In some cases, the whole amount may be supplied to the second distillation column 25.

The recycle liquid 22 includes reaction products such as n-propyl acetate, as well as unreacted allyl acetate, by-products, and the like. Furthermore, the feed gas 23 that is supplied to the hydrogenation reactor 21 may include an inert diluent gas such as nitrogen or a rare gas if necessary, in addition to hydrogen gas. The term "solvent inert to hydrogenation reac tions" refers to a solvent that substantially has no effect on the hydrogenation reaction of allyl acetate.

[Chem. 2]

$$CH_2=CH-CH_2-OCOCH_3+H_2 \rightarrow CH_3-CH_2-CH_2-OCOCH_3 \quad (2)$$

The aforementioned raw material liquid provided to the hydrogenation reactor 21 in the invention is required to be such that the concentration of a formyl group (—CHO)-containing compound and the concentration of an acryloyloxy group (—O—CO—CH=CH$_2$)-containing compound are 100 ppm by mass or less, respectively.

That is, it is now obvious through the investigations made by the inventors that it is important to suppress the concentrations of an easily polymerizable compound such as a formyl group-containing compound or an acryloyloxy group-containing compound, or a reducing substance in the raw material liquid, from the viewpoint of suppressing deterioration of the hydrogenation catalyst. Particularly, when the hydrogenation reaction is continued for a raw material liquid in which at least one of the concentration of a formyl group-containing compound and the concentration of an acryloyloxy group-containing compound exceeds 100 ppm by mass, the polymerization product covers the surface of the hydrogenation catalyst and consequently lowers the catalytic activity. When the catalytic activity is lowered, the conversion rate of allyl acetate is decreased, and as a result, the substrate allyl acetate or 1-propenyl acetate (cis-form and trans-form) resulting from isomerization of allyl acetate come to coexistence in the reaction product liquid. Allyl acetate or 1-propenyl acetate (cis-form and trans-form) has a small difference in boiling point compared with n-propyl acetate, and therefore, it is difficult to separate them by distillation, while it is difficult to separate and purify these during the purification processes carried out later. As a result, the purity of n-propyl acetate as a final product is decreased.

The concentration of the formyl group-containing compound and the concentration of the acryloyloxy group-containing compound are determined by analyzing the raw material liquid by gas chromatography (GC).

The formyl group-containing compound is a so-called aldehyde compound, and specific examples include acrolein, propionaldehyde and 2-methylcrotonaldehyde. The acryloyloxy group-containing compound is acrylic acid or an ester thereof, and specific examples include acrylic acid and allyl acrylate.

When a plurality of the formyl group-containing compound is present, the total concentration is set to 100 ppm by mass or less in the raw material liquid, and also when a plurality of the acryloyloxy group-containing compound is present, the total concentration is set to 100 ppm by mass or less in the raw material liquid. Practically, the concentration is set to 0.01 ppm by mass to 100 ppm by mass. The concentration of the formyl group-containing compound and the concentration of the acryloyloxy group-containing compound in the raw material liquid are each independently preferably 0 ppm by mass to 80 ppm by mass, and more preferably 0 ppm by mass to 50 ppm by mass.

The method of adjusting the concentration of the formyl group-containing compound and the concentration of the acryloyloxy group-containing compound in the raw material liquid respectively to 100 ppm by mass or less, may include a method of adjusting the reaction conditions for the allyl acetate production process, a method of adjusting the distillation conditions (temperature, number of trays, number of distillation columns, and the like) of the first distillation column 17, a method of adjusting the amount of the diluting solvent used, and the like. These concentrations may be respectively adjusted to 100 ppm by mass or less by appropriately combining these methods, or the like.

An example of the method of reducing the amount of the formyl group-containing compound and the acryloyloxy group-containing compound by means of the conditions of the distillation column will be described below.

First, the concentration of impurities in the allyl acetate-containing liquid 20 obtained from a column middle tray can be decreased by increasing the reflux ratio or increasing the pull-out amount at the top or the bottom of the column, as the operating conditions of the first distillation column 17. Furthermore, examples of the solution method in terms of facilities include a method of increasing the number of trays in the column, a method of employing internals having high tray efficiency, a method of setting the position of pull-out of the allyl acetate-containing liquid 20 to an appropriate tray number, and a method of providing a plurality of distillation columns to increase the degree of purification. Of course, since excessive facilities or inefficient operation conditions may decrease the economic efficiency, it is necessary to find the optimal conditions.

Furthermore, incorporating an extraction column, or using other separation processes which those ordinarily skilled in the art can conceive, for example, an adsorption process or a membrane separation process, can also be considered.

For example, when a liquid in which the composition of the raw material supplied to the first distillation column 17 includes 64% by mass of allyl acetate, 22% by mass of acetic acid, 13% by mass of water and which contains 500 ppm by mass of propionaldehyde and 440 ppm by mass of acrolein as the formyl group-containing compounds, and 4500 ppm by mass of allyl acrylate and 2000 ppm by mass of acrylic acid, can be converted such that the concentrations of the formyl group-containing compounds and the acryloyloxy group-containing compounds in the middle tray pull-out liquid are 100 ppm by mass to 1000 ppm by mass, by setting the actual tray number to 60, the oil layer reflux ratio at 130, the aqueous layer reflux ratio at 3, and D/F (=middle tray pull-out amount/distillation column feed amount) to 0.6. Furthermore, when more distillation columns are provided, or the liquid is diluted with the recycle liquid 22 or the like, the concentrations of the formyl group-containing compounds and the acryloyloxy group-containing compounds at the time point of being supplied to the hydrogenation reactor 21 can be adjusted to 100 ppm by weight or less.

In the explanations given above, an instance of mixing the allyl acetate-containing liquid 20 thus obtained with the recycle liquid 22 and a diluting solvent and taking the mixture as a raw material liquid has been illustrated. However, it is not necessarily required to mix the allyl acetate-containing liquid 20 with the recycle liquid 22 and a diluting solvent, and the allyl acetate-containing liquid may be mixed only with the recycle liquid 22 to be used as a raw material liquid, or may be mixed only with a diluting solvent to be used as a raw material liquid. The allyl acetate-containing liquid alone may be used as a raw material liquid, without being mixed with these liquids. In any of these cases, it is important to adjust the concentration of the formyl group-containing compound and the concentration of the acryloyloxy group-containing compound in the raw material liquid respectively to 100 ppm by mass or less at the time point of being supplied to the hydrogenation reactor 21.

However, from the viewpoint of lowering the reaction temperature of the hydrogenation reaction of allyl acetate, it is preferable to carry out the hydrogenation reaction after diluting the reaction liquid with a diluting solvent. That is, in the hydrogenation reaction of allyl acetate, a lower reaction temperature is preferable because it is easy to suppress a hydrogenolysis reaction. Since hydrogenation reactions have very large amounts of heat generation (for example, the amount of heat generation accompanying the hydrogenation of 1 kg of allyl acetate is 1607 kJ), when only allyl acetate is reacted, the temperature in the reaction system markedly increases due to the heat generation accompanying the hydrogenation reaction. This may bring about a possibility of accelerating a hydrogenolysis reaction. In order to suppress this extreme rise in temperature, it is preferable to carry out the hydrogenation reaction after diluting allyl acetate with a diluting solvent that is inert to hydrogenation reactions.

The concentration of allyl acetate in the raw material liquid at the time point of being supplied to the hydrogenation reactor 21 is preferably in the range of 1% by mass to 50% by mass, more preferably in the range of 3% by mass to 30% by mass, and most preferably in the range of 5% by mass to 15% by mass.

If the concentration of allyl acetate is less than 1% by mass, the extreme rise in temperature caused by heat generation can be sufficiently suppressed; however, when the concentration of allyl acetate is excessively lowered, productivity is decreased as a result. On the other hand, if the concentration of allyl acetate exceeds 50% by mass, it is difficult to sufficiently suppress the extreme rise in temperature caused by heat generation. Moreover, in the case of employing an adiabatic liquid phase reaction (particularly, an adiabatic gas-liquid two-phase flow-type liquid phase reaction), there will be an increased likelihood of inability to control the temperature inside the reactor (for example, the temperature inside the reactor cannot be controlled to a suitable range of 0° C. to 200° C.).

Although there are no particular limitations on such diluting solvent, an organic solvent which does not have any ethylenic carbon double-bond (C=C bonds) is preferable from the viewpoint of being less susceptible to hydrogenation reactions.

Specific examples thereof include saturated esters such as ethyl acetate, n-propyl acetate, butyl acetate, isopropyl acetate, n-propyl propionate, ethyl propionate, butyl propionate and isopropyl propionate; hydrocarbons such as cyclohexane, n-hexane and n-heptane; aromatic hydrocarbons such as benzene and toluene; ketones such as acetone and methyl ethyl ketone; halogenated hydrocarbons such as carbon tetrachloride, chloroform, methylene chloride and methyl chloride; ethers such as diethyl ether or di-n-propyl ether; alcohols such as ethanol, n-propanol, isopropanol, n-butanol and sec-butanol; and amides such as N-methyl-2-pyrrolidone and N,N-dimethylacetoamide. Among these, saturated esters, hydrocarbons and ketones are preferable from the viewpoint of being less susceptible to hydrogenation reactions and being less likely to cause hydrogenolysis of allyl acetate.

Furthermore, since n-propyl acetate produced by the reaction is inert to the hydrogenation reaction, the recycle liquid 22 containing this compound can also be used as a diluting solvent.

There are no particular limitations on the hydrogen gas used in the feed gas 23. Normally, commercially available hydrogen gas may be used, but it is preferable to use hydrogen gas with high purity. Nevertheless the amount of hydrogen gas supplied is preferably equal to or greater than the theoretical amount of hydrogen gas required to produce n-propyl acetate from allyl acetate. The amount supplied is more preferably in the range of 1.1- to 3.0-fold the molar theoretical amount, and particularly preferably in the range of 1.1- to 2.0-fold the molar theoretical amount. If the amount of hydrogen gas supplied is equal to or less than the theoretical amount, in the case where side reactions such as a hydrogenolysis reaction occur, the amount of hydrogen consumed by side reactions causes a shortage of hydrogen in the original reaction. In addition, if the amount of hydrogen gas supplied is excessively large, it is economically disadvantageous.

As the hydrogenation catalyst, a catalyst containing an element selected from the elements of Group 8, Group 9 and Group 10 of the Periodic Table (according to the International Union of Pure and Applied Chemistry, Inorganic Chemistry Nomenclature, Revised Edition (1989); hereinafter, the same applies), namely, iron, ruthenium, osmium, cobalt, rhodium, indium, nickel, palladium or platinum, is preferable. Preferable examples of the element include palladium, rhodium, ruthenium, nickel and platinum, and among them, palladium, rhodium and ruthenium are particularly preferable.

The hydrogenation catalyst may be used alone as individual elements (or compounds), or may be supported onto a carrier as necessary. In the case of a hydrogenation reaction carried out using a fixed bed reaction apparatus, which will be described later, a catalyst supported on a carrier is more preferable in view of obtaining a large metal surface area during the contact between the hydrogenation catalyst and allyl acetate.

A material normally used as a carrier for catalyst supporting (for example, a porous material) can be used as the carrier for hydrogenation catalysts, without any particular limitation.

Specific preferable examples of such a carrier include silica, alumina, titanium oxide, diatomaceous earth, carbon, and mixtures thereof.

When these carriers are molded into a pellet form or a spherical form, handling is convenient, which is preferable.

Although there are no particular limitations on the specific surface area of the carrier, it is preferable to use a carrier having a large specific surface area, from the viewpoint of facilitating satisfactory dispersion of the catalytic metal. More specifically, the value of the specific surface area as determined according to the BET method is preferably 10 $mm^2/g$ to 1000 $mm^2/g$, more preferably 30 $m^2/g$ to 800 $m^2/g$, and particularly preferably 50 $m^2/g$ to 500 $m^2/g$. Furthermore, although there are also no particular limitations, the total pore volume of the carrier is preferably 0.05 ml/g to 6.5 ml/g, and more preferably 0.1 ml/g to 5.0 ml/g (particularly, 0.5 ml/g to 3.0 ml/g).

There are no particular limitations on the shape of the carrier, and the shape can be suitably selected from commonly known shapes. From the viewpoint of uniformity of the pressure inside the hydrogenation reactor 21, a pellet form, a spherical form, a hollow cylindrical form, a spoke wheel shape, a honeycomb type monolithic catalyst carrier having parallel flow channels, or an expanded ceramic carrier with an open pore system is preferable, and a pellet shape or a spherical shape is particularly preferable in view of the convenience of the method of production.

When the catalyst supported on a carrier is bulk loaded into a catalyst bed, the carrier can be used without an excessively large decrease in the pressure, and when bulk loaded, it is preferable that the carrier has a very large geometrical surface area as compared with the total volume of bulk loading. In view of these points, the carrier preferably has an external size in the range of 0.5 to 5.0 mm, and more preferably in the range of 1.0 to 4.5 mm.

The hydrogenation reaction can be carried out in the form of any of a gas phase reaction and a liquid phase reaction.

In the case of a gas phase reaction, a fixed bed type reaction apparatus, a moving bed type reaction apparatus, a fluidized bed type reaction apparatus and the like can be used for the structural form of the hydrogenation reactor 21, but a fixed bed reaction apparatus is most generally used.

In the case of performing a gas phase reaction, it is preferable to take the following matters into consideration. In general, the heat of reaction accompanying hydrogenation is extremely high. Furthermore, in the case of a gas phase reaction, the temperature upon the introduction of a reactive substance into the hydrogenation reactor 21 is set to be a temperature equal to or higher than the boiling point of the reactive substance. In this case, if an attempt is made to increase the space-time yield, the amount of heat generation accompanying the hydrogenation increases, and the temperature inside the hydrogenation reactor 21 rises beyond a suitable reaction temperature (for example, 200° C.), and there is a concern that the hydrogenolysis reaction as a side reaction may be accelerated. As a countermeasure for this, the amount of heat generation is suppressed by lowering the space-time yield, or by controlling the temperature by cooling or the like.

In this regard, in the case of performing a liquid phase reaction, the temperature upon the introduction of a reactive substance into the hydrogenation reactor 21 can be set to be lower than the boiling point thereof, and accordingly, there is an advantage in that it is easy to maintain a suitable reaction temperature (for example, 200° C. or lower).

In the case of a liquid phase reaction, specific examples of the structural form of the hydrogenation reactor 21 include a fixed bed type, a fluidized bed type, and an agitated bed type. From the viewpoint of the ease of separation of the catalyst after reaction and the product, a fixed bed reaction apparatus is the most preferable among those.

The hydrogenation reaction uses hydrogen gas, since the method of flowing of a fluid in a liquid phase reaction using a fixed bed type reaction apparatus involves a gas-liquid two-phase flow composed of a liquid containing the raw materials and a gas containing hydrogen gas. The gas-liquid two-phase flow can be divided into three types consisting of a gas-liquid counter-current type, a gas-liquid downward co-current type and a gas-liquid upward co-current type, based on the manner of flow of the raw material gas and liquid. Although any of these can be used in the invention, a gas-liquid downward co-current type is the most preferable from the viewpoint of allowing efficient contact between the hydrogen and catalyst required for the reaction.

In summary of the above, from the viewpoint of increasing the space-time yield while suppressing hydrogenolysis, the most preferable reaction type for the hydrogenation reactor 21 is a liquid phase reaction of gas-liquid two-phase flow type, and the manner of the fluid flow thereof is the gas-liquid downward co-current type.

In the case of carrying out a liquid phase reaction of gas-liquid two-phase flow type, it is preferable to carry out the hydrogenation reaction in the form of an adiabatic liquid phase reaction by using a raw material liquid that has been diluted with the diluting solvents described above, from the viewpoint of suppressing a hydrogenolysis reaction. Thereby, the allyl acetate concentration in the raw material liquid can be lowered, and measures such as cooling the hydrogenation reactor 21 are unnecessary.

There are no particular limitations on the form of the hydrogenation reactor 21. In the case of using a reaction form of gas-liquid downward co-current type using a fixed bed reaction apparatus, it is preferable to use a reactor equipped with a cooling jacket, a multitubular reaction apparatus equipped with a cooling jacket, or an adiabatic reaction apparatus. An adiabatic reaction apparatus is preferable from the viewpoint of the construction cost of the hydrogenation reactor 21, the conversion rate of allyl acetate, or the like.

The reaction temperature of the hydrogenation reaction may vary with the type of the raw materials, but the reaction temperature is preferably 0° C. to 200° C., and particularly preferably 40° C. to 150° C. If the reaction temperature is lower than 0° C., it tends to be difficult to obtain a sufficient reaction rate, while if the temperature exceeds 200° C., hydrogenolysis tends to occur easily.

In the case of performing a gas phase reaction, the reaction pressure of the hydrogenation reaction is such that sufficient activity is obtained even at normal pressure. Consequently, it is preferable to carry out the reaction at normal pressure. However, if the pressure is high to an extent that allyl acetate can vaporize at a temperature of 200° C. or lower, the reaction can be accelerated under pressurized conditions, as necessary.

On the other hand, in the case of performing a liquid phase reaction of gas-liquid two-phase flow type, it is preferable to pressurize the reaction from the viewpoint of securing a dissolved hydrogen concentration. From the viewpoint of securing a sufficient hydrogen concentration in the reactor during the liquid phase reaction of gas-liquid two-phase flow type, the manner of flowing the raw material gas and liquid preferably involves the gas-liquid downward co-current type as previously described.

In the case of performing a liquid phase reaction of gas-liquid two-phase flow type, the reaction pressure is preferably in the range of 0.05 MPaG to 10 MPaG, and more preferably in the range of 0.3 MPaG to 5 MPaG. If the reaction pressure is lower than 0.05 MPaG, it tends to be difficult for the hydrogenation reaction to be sufficiently accelerated, while on the other hand, if the reaction pressure exceeds 10 MPaG, hydrogenolysis reaction tends to occur easily.

From the viewpoint of securing a sufficient hydrogen concentration inside the hydrogenation reactor 21, the reaction form of gas-liquid downward co-current type as previously described is the most preferable.

<Purification of N-Propyl Acetate>

The hydrogenation reaction liquid 24 obtained from the hydrogenation reactor 21 is supplied to the second distillation column 25. Then, the second distillation column bottom liquid 26 containing a high concentration of high-boiling point components such as acetic acid and propyl propionate, and the second distillation column top liquid 27 containing more of low-boiling point components such as C3 gas, propionaldehyde and water are respectively pulled out, and a high purity n-propyl acetate product 28 is pulled out from the column middle tray of the second distillation column 25. A high purity n-propyl acetate product 28 can be obtained in this manner.

As it has been described in detail, in the case of producing n-propyl acetate by subjecting a raw material liquid containing allyl acetate to a hydrogenation reaction, when the concentration of a formyl group-containing compound and the concentration of an acryloyloxy group-containing compound in the raw material liquid are respectively set to 100 ppm by mass or less, deterioration of a hydrogenation catalyst is suppressed, and the catalytic activity can be maintained. The method for producing n-propyl acetate of the invention is particularly useful when a high purity allyl acetate-containing liquid obtained by purifying a crude allyl acetate liquid obtained from propylene, oxygen and acetic acid through a purification process such as distillation, is used as a raw material liquid.

EXAMPLES

Hereinafter, the invention will be described more specifically with reference to Examples and Comparative Examples, but the invention is not intended to be limited to these Examples.

The definitions of terms used in Examples and Comparative Examples are as follows.

Yield (%)=(Mole number of n-propyl acetate produced)/(Mole number of allyl acetate introduced into the reactor)×100

Yield retention ratio (%)=Yield after a lapse of 100 hours from the initiation of reaction/Yield after a lapse of 3 hours from the initiation of reaction×100

The composition ratio of the condensed liquid obtained in the respective Examples shown below was determined by gas chromatography (GC). The measurement conditions are shown below.

(GC Conditions)

Instrument: GC-17A (manufactured by Shimadzu Corp.)

Detector: Hydrogen flame ionization detector

Measurement method: Internal standard method (internal standard substance: 1,4-dioxane)

Injection temperature: 200° C.

Heating conditions: maintained for 10 minutes at 40° C., followed by heating at a rate of 5° C./minute, and maintained for 30 minutes at 200° C.

Column: TC-WAX (manufactured by GL Science, Inc.), internal diameter: 0.25 mm, film thickness: 0.25 μm, length: 30 m The reagents used in the reaction include the following substances Allyl acetate: Manufactured by Showa Denko K.K., purity 99.6%, 1-propenyl acetate 3594 ppm, acetic acid 151 ppm, water 59 ppm n-propyl acetate: Manufactured by Kishida Chemical Co., Ltd., purity 99.7%, isopropyl acetate 459 ppm, n-propanol 2696 ppm, water 170 ppm Acrolein: Manufactured by Tokyo Chemical Industry Co., Ltd., purity>90%

Propionaldehyde: Manufactured by Wako Pure Chemical Industries, Ltd., purity 98+%

2-Methylcrotonaldehyde: Manufactured by Tokyo Chemical Industry Co., Ltd., purity>95%

Acrylic acid: Manufactured by Wako Pure Chemical Industries, Ltd., purity 98+%

Allyl acrylate: Manufactured by Alfa Aesar GmbH, purity 90+%

Example 1

Figure 2:
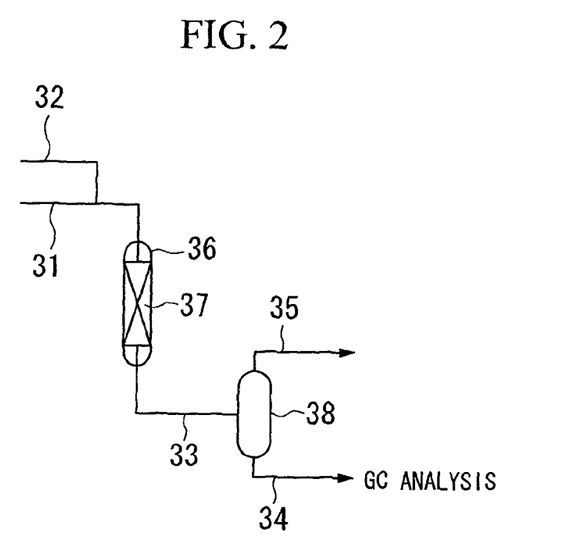
FIG. 2 is a process flow diagram showing the process for producing n-propyl acetate by subjecting a raw material liquid containing allyl acetate to a hydrogenation reaction in the Examples.

In the flow diagram shown in FIG. 2, 80 cc of a supported type palladium catalyst (alumina support, pellets having a diameter of 3 mm×a length of 3 mm, palladium content 0.3% by mass, "PGC Catalyst" manufactured by N.E. Chemcat Corp.) was packed as a hydrogenation catalyst in a stainless steel cylindrical reactor 36 (internal volume 80 cc) having an inner diameter of 20 mmφ to be used as a catalyst packed bed 37, and the pressure in the reactor 36 was adjusted to 0.8 MPaG with hydrogen gas. Hydrogen gas was passed through the reactor 36 from a hydrogen gas supply pipe 32 at a rate of 16.6 Nl/hr, and the electrical furnace set temperature in the reactor 36 was set at 80° C. Then, a mixed liquid of n-propyl acetate:allyl acetate=9:1 (vol%) as a reaction feed liquid (raw material liquid) was passed through the reactor 36 from the top of the reactor 36 through a liquid supply pipe 31 at a rate of 400 cc/hr (fixed bed type, gas-liquid downward co-current type).

The reaction feed liquid did not contain various substances such as acrolein, propionaldehyde, 2-methylcrotonaldehyde, acrylic acid and allyl acrylate, and their concentration was 0 ppm by mass.

Figure 3:
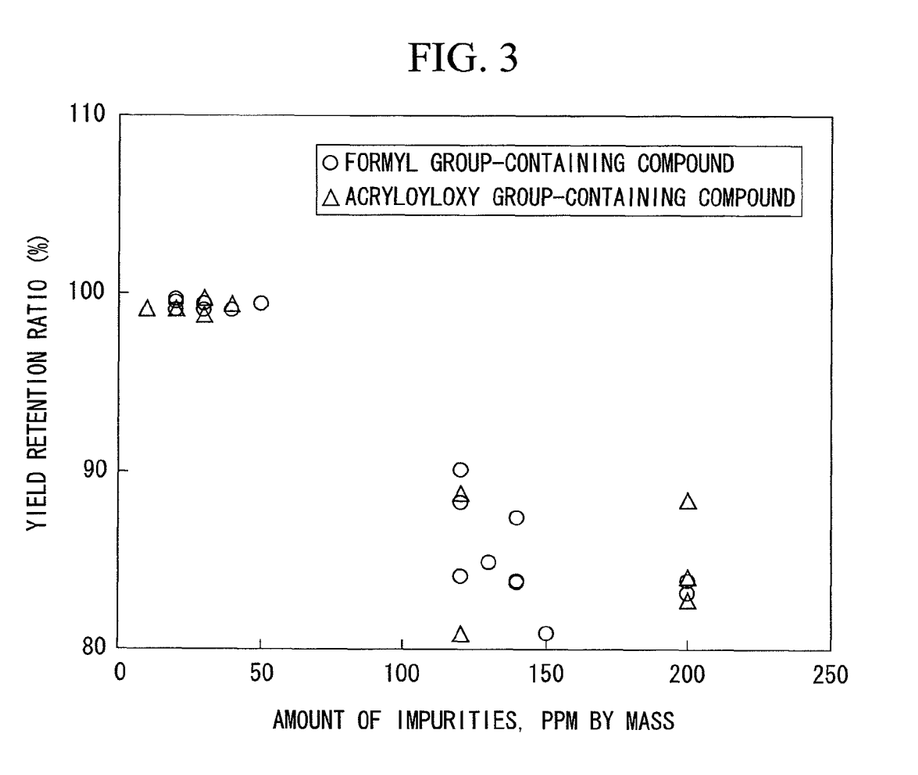
FIG. 3 is a graph obtained by plotting the yield retention ratio against the amount of impurities in the reaction feed liquid.

The reaction mixture obtained from a reactor outlet gas 33 was condensed in a condenser 38, and the condensed liquid 34 thus obtained was analyzed using GC under the conditions mentioned above. Reference numeral 35 in the figure refers to a non-condensed gas. The yield obtained after a lapse of 3 hours from the initiation of reaction and the yield obtained after a lapse of 100 hours are shown in Table 1. The ratio of the yield obtained after a lapse of 100 hours from the initiation of reaction to the yield obtained after a lapse of 3 hours from the initiation of reaction was defined as the yield retention ratio, expressed as a percentage. The yield retention ratio was plotted against the amount of impurities added to the reaction feed liquid, that is, the concentration of a formyl group-containing compound and an acryloyloxy group-containing compound (FIG. 3)

Example 2

Allyl acetate was hydrogenated in the same manner as in Example 1, except that a supported type palladium catalyst (palm shell activated carbon carrier, pulverization product (4 to 8 meshes), palladium content 0.5% by mass, "0.5% Pd-Carbon Grain (W) LA type" manufactured by N.E. Chemcat Corp.) was used as the hydrogenation catalyst. The results are shown in Table 1 and FIG. 3.

Example 3

Allyl acetate was hydrogenated in the same manner as in Example 1, except that a supported type platinum catalyst (alumina carrier, pellets having a diameter of 3 mm×a length of 3 mm, platinum content 0.3% by mass, "HDMax800Tab" manufactured by SÜD Chemie Catalysts, Inc.) was used as the hydrogenation catalyst. The results are shown in Table 1 and FIG. 3.

Example 4

Allyl acetate was hydrogenated in the same manner as in Example 1, except that a supported type nickel catalyst (diatomaceous earth carrier, cylindrically shaped molded product having a diameter of 5.2 mm×a length of 4.6 mm, nickel content 50% by mass, "N111" manufactured by Nikki Chemical Co., Ltd.) was used as the hydrogenation catalyst. The results are shown in Table 1 and FIG. 3.

Example 5

Allyl acetate was hydrogenated in the same manner as in Example 1, except that 20 ppm by mass of acrolein was incorporated into the mixed liquid of n-propyl acetate:allyl acetate=9:1 (vol %) as a reaction feed liquid. The results are shown in Table 1 and FIG. 3.

Examples 6 to 19 and Comparative Example 1 to 13

Allyl acetate was hydrogenated in the same manner as in Example 1, except that the formyl group-containing compounds and acryloyloxy group-containing compounds of the type and amount as indicated in Table 1 were incorporated into the mixed liquid of n-propyl acetate:allyl acetate=9:1 (vol %) to be used as reaction feed liquids, and the catalysts indicated in Table 1 were used. The results are shown in Table 1 and FIG. 3 (however, Example 19 is not shown in FIG. 3).

TABLE 1

| | | Amount of impurities in reaction feed liquid (ppm by mass) | | | | | Yield (%) | |
|---|---|---|---|---|---|---|---|---|
| | | Formyl group-containing compound | | | Acryloyloxy group-containing compound | | Hours passed from initiation of reaction (hr) | |
| | Hydrogenation catalyst | ACR | PALD | MCAD | AA | ALAc | 3 | 100 |
| Example1 | PGC Catalyst | 0 | 0 | 0 | 0 | 0 | 99.2 | 99.1 |
| Example2 | Pd-Carbon | 0 | 0 | 0 | 0 | 0 | 99.3 | 99.3 |
| Example3 | HDMax | 0 | 0 | 0 | 0 | 0 | 97.5 | 97.4 |
| Example4 | N111 | 0 | 0 | 0 | 0 | 0 | 98.0 | 98.0 |
| Example5 | PGC Catalyst | 20 | | | | | 99.0 | 98.1 |
| Example6 | PGC Catalyst | | 20 | | | | 99.0 | 98.5 |
| Example7 | PGC Catalyst | | | 20 | | | 99.1 | 98.6 |
| Example8 | PGC Catalyst | | | | 20 | | 99.0 | 98.2 |
| Example9 | PGC Catalyst | | | | | 20 | 99.1 | 98.3 |
| Example10 | PGC Catalyst | 20 | | 10 | | | 98.9 | 98.3 |
| Example11 | PGC Catalyst | 30 | 10 | | | | 99.0 | 98.1 |
| Example12 | PGC Catalyst | | | | 20 | 20 | 98.8 | 98.2 |
| Example13 | Pd-Carbon | 30 | 20 | | | | 99.2 | 98.6 |
| Example14 | Pd-Carbon | | | | 10 | 20 | 99.1 | 97.9 |
| Example15 | HDMax | 20 | | | | | 97.2 | 96.9 |
| Example16 | HDMax | | | | 30 | | 97.4 | 97.2 |
| Example17 | N111 | 30 | | | | | 97.8 | 96.9 |
| Example18 | N111 | | | | 10 | | 97.9 | 97.1 |
| Example19 | PGC Catalyst | 30 | | | | 20 | 98.9 | 98.2 |
| Comparative Example1 | PGC Catalyst | 120 | | | | | 98.9 | 87.3 |
| Comparative Example2 | PGC Catalyst | 200 | | | | | 98.9 | 82.2 |
| Comparative Example3 | PGC Catalyst | | 120 | | | | 99.0 | 89.2 |

TABLE 1-continued

| | | Amount of impurities in reaction feed liquid (ppm by mass) | | | | | Yield (%) | |
|---|---|---|---|---|---|---|---|---|
| | | Formyl group-containing compound | | | Acryloyloxy group-containing compound | | Hours passed from initiation of reaction (hr) | |
| | Hydrogenation catalyst | ACR | PALD | MCAD | AA | ALAc | 3 | 100 |
| Comparative Example4 | PGC Catalyst | 90 | 50 | | | | 98.4 | 86.0 |
| Comparative Example5 | PGC Catalyst | | | 130 | | | 99.2 | 84.2 |
| Comparative Example6 | PGC Catalyst | | | 120 | | | 98.2 | 87.2 |
| Comparative Example7 | PGC Catalyst | | | | | 200 | 98.0 | 81.1 |
| Comparative Example8 | PGC Catalyst | | | | 80 | 50 | 98.5 | 87.1 |
| Comparative Example9 | PGC Catalyst | 90 | 50 | | | | 99.1 | 83.1 |
| Comparative Example10 | PGC Catalyst | | | 150 | 130 | | 99.0 | 80.1 |
| Comparative Example11 | Pd-Carbon | 200 | | | | | 99.1 | 83.1 |
| Comparative Example12 | HDMax | 140 | | | | | 96.9 | 81.1 |
| Comparative Example13 | N111 | 120 | | | 120 | | 97.9 | 82.3 |

PGC: PGC catalyst
Pd-Carbon: 0.5% Pd-carbon particles
HDMax: HDMax800Tab
N111: N111
ACR: Acrolein
PALD: Propionaldehyde
MCAD: 2-Methylcrotonaldehyde
AA: Acrylic acid
ALAc: Allyl acrylate As is obvious from Table 1 and FIG. 3, according to the respective Examples in which the concentration of the formyl group-containing compound and the concentration of the acryloyloxy group-containing compound in the raw material liquid (reaction feed liquid) were respectively set at 100 ppm by mass or less, there was almost no decrease in yield even after a lapse of 100 hours from the initiation of reaction, and deterioration of the hydrogenation catalyst was suppressed.

Industrial Applicability

The invention can be applied to a method for producing n-propyl acetate by a hydrogenation reaction of a raw material liquid containing allyl acetate.

Reference Signs List

| 11: | REACTOR |
|---|---|
| 12: | REACTOR OUTLET GAS |
| 13: | CONDENSED COMPONENT SEPARATION TANK |
| 14: | CRUDE ALLYL ACETATE LIQUID |
| 15: | NON-CONDENSED COMPONENT |
| 16: | OIL-WATER SEPARATION TANK |
| 17: | FIRST DISTILLATION COLUMN |
| 18: | FIRST DISTILLATION COLUMN BOTTOM LIQUID |
| 19: | FIRST DISTILLATION COLUMN TOP LIQUID |
| 20: | ALLYL ACETATE-CONTAINING LIQUID |
| 21: | HYDROGENATION REACTOR |
| 22: | RECYCLE LIQUID |
| 23: | FEED GAS |
| 24: | HYDROGENATION REACTION LIQUID |
| 25: | SECOND DISTILLATION COLUMN |
| 26: | SECOND DISTILLATION COLUMN BOTTOM LIQUID |
| 27: | SECOND DISTILLATION COLUMN TOP LIQUID |
| 28: | N-PROPYL ACETATE PRODUCT |
| 31: | LIQUID SUPPLY PIPE |
| 32: | HYDROGEN GAS SUPPLY PIPE |
| 33: | REACTOR OUTLET GAS |
| 34: | CONDENSED LIQUID |
| 35: | NON-CONDENSED GAS |
| 36: | STAINLESS STEEL CYLINDRICAL REACTOR |
| 37: | CATALYST-PACKED BED |
| 38: | CONDENSER |

The invention claimed is:

1. A method for producing n-propyl acetate, comprising subjecting a raw material liquid containing allyl acetate, 100 ppm by mass or less of a formyl group-containing compound, and 100 ppm by mass or less of an acryloyloxy group-containing compound to a hydrogenation reaction.

2. The method for producing n-propyl acetate according to claim 1, wherein the raw material liquid contains an allyl acetate-containing liquid which is produced from propylene, oxygen and acetic acid.

3. The method for producing n-propyl acetate according to claim 1, wherein the formyl group-containing compound is at least one selected from acrolein, propionaldehyde and 2-methylcrotonaldehyde.

4. The method for producing n-propyl acetate according to claim 1, wherein the acryloyloxy group-containing compound is acrylic acid and/or allyl acrylate.

5. The method for producing n-propyl acetate according to claim 1, wherein the hydrogenation reaction uses, as a hydrogenation catalyst, a compound containing at least one element selected from the group consisting of the elements of Group 8, Group 9 and Group 10 in the Periodic Table.

6. The method for producing n-propyl acetate according to claim 5, wherein the hydrogenation catalyst is a compound containing at least one selected from the group consisting of palladium, rhodium, ruthenium, nickel and platinum.

7. The method for producing n-propyl acetate according to claim 2, wherein the formyl group-containing compound is at least one selected from acrolein, propionaldehyde and 2-methylcrotonaldehyde.

8. The method for producing n-propyl acetate according to claim 2, wherein the acryloyloxy group-containing compound is acrylic acid and/or allyl acrylate.

9. The method for producing n-propyl acetate according to claim 2, wherein the hydrogenation reaction uses, as a hydrogenation catalyst, a compound containing at least one element selected from the group consisting of the elements of Group 8, Group 9 and Group 10 in the Periodic Table.

10. The method for producing n-propyl acetate according claim 3, wherein the hydrogenation reaction uses, as a hydrogenation catalyst, a compound containing at least one element selected from the group consisting of the elements of Group 8, Group 9 and Group 10 in the Periodic Table.

11. The method for producing n-propyl acetate according claim 4, wherein the hydrogenation reaction uses, as a hydrogenation catalyst, a compound containing at least one element selected from the group consisting of the elements of Group 8, Group 9 and Group 10 in the Periodic Table.

12. The method for producing n-propyl acetate according claim 7, wherein the hydrogenation reaction uses, as a hydrogenation catalyst, a compound containing at least one element selected from the group consisting of the elements of Group 8, Group 9 and Group 10 in the Periodic Table.

13. The method for producing n-propyl acetate according claim 8, wherein the hydrogenation reaction uses, as a hydrogenation catalyst, a compound containing at least one element selected from the group consisting of the elements of Group 8, Group 9 and Group 10 in the Periodic Table.

14. The method for producing n-propyl acetate according to claim 9, wherein the hydrogenation catalyst is a compound containing at least one selected from the group consisting of palladium, rhodium, ruthenium, nickel and platinum.

15. The method for producing n-propyl acetate according to claim 10, wherein the hydrogenation catalyst is a compound containing at least one selected from the group consisting of palladium, rhodium, ruthenium, nickel and platinum.

16. The method for producing n-propyl acetate according to claim 11, wherein the hydrogenation catalyst is a compound containing at least one selected from the group consisting of palladium, rhodium, ruthenium, nickel and platinum.

17. The method for producing n-propyl acetate according to claim 12, wherein the hydrogenation catalyst is a compound containing at least one selected from the group consisting of palladium, rhodium, ruthenium, nickel and platinum.

18. The method for producing n-propyl acetate according to claim 13, wherein the hydrogenation catalyst is a compound containing at least one selected from the group consisting of palladium, rhodium, ruthenium, nickel and platinum.

* * * * *